US011071765B2

(12) United States Patent
Gokaraju et al.

(10) Patent No.: US 11,071,765 B2
(45) Date of Patent: Jul. 27, 2021

(54) **HERBAL COMPOSITIONS COMPRISING EXTRACTS OF *BACOPA MONNIERI* AND *TERMINADA CHEBULA***

(71) Applicant: LAILA NUTRACEUTICALS, Vijayawada (IN)

(72) Inventors: Ganga Raju Gokaraju, Vijaywada (IN); Rama Raju Gokaraju, Vijayawada (IN); Trimurtulu Golakoti, Vijayawada (IN); Kiran Bhupathiraju, Vijayawada (IN); Krishanu Senguptha, Vijayawada (IN); Venkata Kanaka Ranga Raju Gokaraju, Vijayawada (IN); Venkata Krishna Raju Alluri, Vijayawada (IN)

(73) Assignee: LAILA NUTRACEUTICALS, Vijayawada (IN)

( * ) Notice: Subject to any disclaimer, the term of this patent is extended or adjusted under 35 U.S.C. 154(b) by 0 days.

(21) Appl. No.: 16/349,518

(22) PCT Filed: Nov. 11, 2017

(86) PCT No.: PCT/IN2017/050522
§ 371 (c)(1),
(2) Date: May 13, 2019

(87) PCT Pub. No.: WO2018/087782
PCT Pub. Date: May 17, 2018

(65) Prior Publication Data
US 2019/0336555 A1 Nov. 7, 2019

(30) Foreign Application Priority Data
Nov. 11, 2016 (IN) .............................. 201641038595

(51) Int. Cl.
*A61K 36/68* (2006.01)
*A23L 33/105* (2016.01)
*A61K 36/80* (2006.01)
*A61K 45/06* (2006.01)

(52) U.S. Cl.
CPC ............ *A61K 36/68* (2013.01); *A23L 33/105* (2016.08); *A61K 36/80* (2013.01); *A61K 45/06* (2013.01)

(58) Field of Classification Search
None
See application file for complete search history.

(56) References Cited

U.S. PATENT DOCUMENTS

| 2004/0156920 | A1* | 8/2004 | Kane | A01N 65/42 424/725 |
|---|---|---|---|---|
| 2006/0193928 | A1 | 8/2006 | Soman et al. | |
| 2009/0192097 | A1 | 7/2009 | Agarwal | |
| 2013/0266676 | A1 | 10/2013 | Ghosal et al. | |
| 2014/0322198 | A1 | 10/2014 | Buchwald-Werner et al. | |
| 2019/0166882 | A1* | 6/2019 | Parachur | A23K 40/10 |
| 2019/0388490 | A1* | 12/2019 | Deo | A61Q 19/00 |

FOREIGN PATENT DOCUMENTS

WO 2016/077454 A1 5/2016

OTHER PUBLICATIONS

Monera, Natural Memory Enhancer by Square Pharma Oct. 27, 2013. Retrieved from www.squarepharma.com.bd (Year: 2013).*
Maity D. et al. An Updated Review on Herbal Drugs: Nootropic Activity and Possible Mechanisms Asian J of Pharmaceutical and Clinical Research 12(6)19-26, 2019. (Year: 2019).*
Kongkeaw C. et al. Meta-Analysis of Randomized Controlled Trials on Cognitive Effects of Bacopa monnieri Extract. J of Ethnopharmacology 151:528-535, 2014. (Year: 2014).*
Kulkarnia R. et al. Rasayana Herbs of Ayurveda to Treat Age Related Cognitive Decline: An Update. Pharmacognosy J 8(5)411-423, Sep./Oct. 2016. (Year: 2016).*

* cited by examiner

*Primary Examiner* — Ralph J Gitomer
(74) *Attorney, Agent, or Firm* — Kramer Amado PC (57) ABSTRACT

The present invention relates to synergistic compositions comprising extracts or fractions derived from *Bacopa monnieri* in combination with extracts or fractions derived from *Terminalia chebula* for improving brain health, memory/mental condition, enhancing brain/mental functions such as cognition, memory, learning, retention, communication and for treating neurodegenerative diseases/disorders such as Alzheimer's disease, Parkinson's disease etc. The invention further relates to method of improving brain health and brain functions selected from cognition, memory, memory retention, information recall, intelligence, motivation, attention, concentration, learning power and communication and to alleviate disease conditions related to cognition and memory deficits in a mammal by supplementing the mammal with an effective dose of the synergistic composition comprising at least one extract or fraction derived from *Bacopa monnieri* in combination with at least extract or fraction derived from *Terminalia chebula*.

16 Claims, 5 Drawing Sheets

HERBAL COMPOSITIONS COMPRISING EXTRACTS OF *BACOPA MONNIERI* AND *TERMINADA CHEBULA*

TECHNICAL FIELD OF THE INVENTION

The present invention relates to synergistic compositions for improving brain health and brain function. In particular the present invention relates to synergistic compositions comprising at least one component selected from extract(s), fraction(s), active compound(s) and phytochemicals or mixtures thereof derived from *Bacopa monnieri* in combination with least one component selected from extract(s), fraction(s), active compound(s) and phytochemicals or mixtures thereof derived from *Terminalia chebula* for improving brain health, memory/mental condition, enhancing brain/mental functions such as cognition, memory, learning, retention, recall information, communication and for treating neurodegenerative diseases such as Alzheimer's disease, Parkinson's disease etc.

BACKGROUND OF THE INVENTION

Age-associated cognitive deficit has been well documented in the scientific literature. Cognitive abilities, such as vocabulary, conceptual reasoning, memory, and processing speed, decline gradually over time. Acetylcholine plays pivotal role in the cognitive function. Acetylcholinesterase, also known as AChE, is the primary cholinesterase in the body. It is an enzyme that catalyzes the breakdown of acetylcholine (ACh) and of some other choline esters that function as neurotransmitters. AChE activity serves to terminate synaptic transmission. During neurotransmission, acetylcholine (Ach) is released from the presynaptic neuron into the synaptic cleft and binds to ACh receptors on the post-synaptic membrane, relaying the signal from the nerve. AChE, also located on the post-synaptic membrane, terminates the signal transmission by hydrolyzing ACh. The liberated choline is taken up again by the pre-synaptic neuron and ACh is synthesized by combining with acetyl-CoA through the action of choline acetyltransferase. Hence, inhibitors of acetylcholinesterase can have important role in improving brain health and functions.

*Bacopa monnieri* of family Plantaginaceae, commonly known as Brahmi, is a nootropic agent that has been widely used in Ayurveda for improving cognition. It is native to the wetlands of southern and Eastern India, Australia, Europe, Africa, Asia, and North and South America.

*Terminalia chebula* of family Combretaceae is commonly known as haritaki and it is native to South Asia. Traditionally *Terminalia chebula* is used for treating flatulence, constipation, diarrhea, dysentery, cyst, digestive disorders, vomiting, enlarged liver and spleen, cough and bronchial asthma, and for metabolic harmony. Bark is used as diuretic. The Ayurvedic Pharmacopoeia of India, along with other therapeutic applications, indicated the use of powder of mature fruits in intermittent fevers, chronic fevers, anemia and polyuria.

Indian Patent Application 3689/MUM/2014, discloses a synergistic composition comprising combination of herbs comprising *Tinospora cordifolia, Withania somnifera, Glycyrrhiza glabra, Convolvulus pluricaulis, Nardostachys jatamansi, Terminalia chebula, Piper nigrum, Cissampelos pareira, Acorus calamus, Moringa oleifera, Bacopa monnieri* and nutraceutical ingredients comprising Vitamin B6, Vitamin B12, Vitamin E, Folate/Folic acid, Zinc and Magnesium, useful for treating tension, anxiety, loss of memory, neurosis, depression conditions, arthritis, impotency, anemia and hepatitis.

Indian Patent application 3344/DEL/2015, discloses an Ayurvedic Rasayan for children brain health comprises of powdered roots of *Hemidesmus indicus*, plant of *Bacopa monnieri*, rhizome of *Acorus calamus*, stem of *Sida cordifolia*, stem of *Abutilon indicum*, plant of *Uraria picta*, bark of *Acacia catechu*, bark of *Terminalia arjuna*, rock salt, rhizome of *Curcuma longa*, Triphala, roots of *Cyperus Rotundus*, ghee, gold particles, wherein Triphala consists of equal parts of fruits without seeds, of *Emblica officinalis, Terminalia bellirica*, and *Terminalia chebula*, Cow's Ghee and colloidal gold particles.

U.S. Pat. No. 8,962,042B2, discloses a method for treating apraxia, autism, speech impairments, traumatic brain injury, seizure disorders, epilepsy, global delays, or ADHD, comprising administering to a patient in need thereof a composition comprising an effective amount of a mixture or purified mixture thereof comprising botanical extracts selected from each of the group of botanicals consisting of *Gymnema sylvestre, Commiphora mukul, Curcuma longa, Camellia sinensis, Emblica officinalis,* and *Terminalia chebula*.

WO 2014085851 A1, discloses methods of improving cognition in human subject, wherein the subject is mentally stressed, mentally fatigued and/or cognitively challenged, using alcoholic extracts of *Bacopa monnieri* extracts.

US 20120034324 A1 provides a process for preparing a herbal formulation for the prevention and management of neurodegenerative disorders comprising, preparing hydromethanolic extract of at least one plant selected from *Curcuma longa, Bacopa monnieri* and *Valeriana jatamansi*, at 70-80° C., maintaining the pH of the solution between 7-10, separating the active compounds chromatographically and subjecting the active compounds to the step of molecular characterization.

US 20090192097 A1, provides a synergistic herbal composition from the plant species *Bacopa monnieri*, comprising bacoside A3 at a concentration ranging from 0.1 to 25% w/w, bacopaside II at a concentration ranging from 0.1 to 25% w/w, jujubogenin isomer of bacopasaponin C at a concentration ranging from 0.1 to 25% w/w, bacopasaponin C at a concentration ranging from 0.1 to 25% w/w, bacopaside I at a concentration ranging from 0.1 to 25% w/w, bacosine at a concentration ranging from 0.1 to 25% w/w, apigenin at a concentration ranging from 0.05 to 5% w/w, sitosterol-D-glucoside at a concentration ranging from 0.05 to 5% w/w, and luteolin at a concentration ranging from 0.05 to 5% w/w for the Management of Neurodegenerative Disorders.

EP 2486932 A1, discloses a synergistic composition comprising extracts of *Terminalia chebula* and *Terminalia bellerica* for improving the cognition.

None of the above prior art articles disclose the synergistic compositions containing an extract or fraction derived from *Bacopa monnieri* in combination with an extract or fraction derived from *Terminalia chebula*.

There is a continuous need in the art to provide highly potent alternative treatments comprising highly effective herbal extracts for improving brain health and brain function. Moreover, there is a need in the art for better treatment options that provide minimal side effects thereby making the option safe for human consumption especially when used in long term therapy.

OBJECT OF THE INVENTION

Therefore the principal object of the present invention is to provide synergistic compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula* for improving brain health and brain functions, which include but not limited to cognition, memory, intelligence, motivation, attention, retention, concentration, learning power and better communication and to alleviate disease conditions related to cognition and memory deficits and the like.

The other principal object of the present invention is to provide synergistic compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula* for enhancing learning and memory, which include but not limited to improved acquisition, improved retention, improved concentration, improved cognitive performance, delayed extinction, mental acuity, and faster reaction, improved memory free recall, improved retention of new information and also decreased the rate of forgetting, improved attention, cognitive processing, and working memory.

The further object of the invention is to provide use of synergistic compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula* for the prevention, control and treatment of memory deficits or to enhance brain health and functions such as cognition, memory, learning, attention, memory retention and communication and neurodegenerative diseases such as Alzheimer's disease, Parkinson's disease etc.

Yet another object of the present invention is to provide methods of improving brain health and brain functions, which include but not limited to cognition, memory, intelligence, motivation, attention, concentration, learning power and better communication and to alleviate disease conditions related to cognition and memory deficits, such as ADHD and the like in a mammal, wherein the method comprises supplementing the mammal with an effective dose of a synergistic composition comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula*.

SUMMARY OF THE INVENTION

The present invention provides novel synergistic compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula* for improving brain health and brain functions, which include but not limited to cognition, memory, intelligence, motivation, attention, concentration, learning power and better communication and to alleviate disease conditions related to cognition and memory deficits and the like. The synergistic compositions may further contain pharmaceutically or nutraceutically acceptable actives, excipients, carriers or diluents.

The other important aspect of the present invention is to provide use of synergistic compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula* to prevent, control and treat brain related diseases/disorders which include but not limited to senile dementia, multi-infarct dementia, dyslexia, aphasia, organic brain syndrome, myasthenia gravis, vascular dementia, mild cognitive impairment (MCI), Lewy body dementia, Wernicke-Korsakoff-syndrome, Alzheimer's disease, Parkinson's disease, Attention-deficit Hyperactivity Disorder (ADHD), hypoxia, anoxia, cerebrovascular insufficiency, epilepsy, myoclonus and hypo cholinergic dysfunctions, to slowdown memory deterioration, functional loss and to treat memory impairment disorders, neurodegenerative disorders, and for controlling blood pressure and blood circulation in the brain.

In another aspect the present invention provides compositions comprising at least one component selected from extract(s), fraction(s), active compound(s) and phytochemicals or mixtures thereof derived from *Bacopa monnieri* and at least one component selected from extract(s), fraction(s), active compound(s) and phytochemicals or mixtures thereof derived from *Terminalia chebula* in combination with at least one component selected from excipients, diluents, biological agent(s) and Nootropic agent(s).

In yet another aspect the present invention provides compositions comprising at least one component selected from extract(s), fraction(s), active compound(s) and phytochemicals or mixtures thereof derived from *Bacopa monnieri* and at least one component selected from extract(s), fraction(s), active compound(s) and phytochemicals or mixtures thereof derived from *Terminalia chebula* in combination with at least one or more agents selected from natural antioxidants, anti-inflammatory agents and immune modulators.

In other aspect the invention provides methods of improving brain health and brain functions, which include but not limited to cognition, memory, recall information, intelligence, motivation, attention, concentration, learning power and better communication and to alleviate disease conditions related to cognition and memory deficits, such as ADHD and the like in a mammal, wherein the method comprises supplementing the mammal with an effective dose of a synergistic composition comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula*.

DESCRIPTION OF THE FIGURES

FIG. 4: A) Effect of LN16026F3 on Target latency (ms)—Acquisition Trial Values are expressed as Mean±S.E.M. n=7 animals/group ##$p<0.01$ and ###$p<0.001$ as compared to normal control group (G1) by Two-way ANOVA followed by Bonferroni post-hoc test. *$p<0.05$, $p<0.01$ and *$p<0.001$ as compared to Scopolamine group (G2) by Two-way ANOVA followed by Bonferroni post-hoc test B) Effect of LN16026F3 on Distance travelled (cm)—Acquisition Trial Values are expressed as Mean±S.E.M. n=7 animals/group #$p<0.05$ as compared to normal control group (G1) by Two-way ANOVA followed by Bonferroni post-hoc test. *$p<0.05$ as compared to Scopolamine group (G2) by Two-way ANOVA followed by Bonferroni post-hoc test C) Effect of LN16026F3 on Dopamine level (ng/mg) in Hippocampus tissue Values are expressed as Mean±S.E.M; n=6-7 animals/group; Statistics performed by One-way ANOVA followed by Dunnett's Test.

B) Effect of LN16026F3 on Target Crossings—Probe Trial

Values are expressed as Mean±S.E.M; n=7 animals/group; #$p<0.05$ as compared Scopolamine group (G2) by One-way ANOVA followed by Dunnett's Test.

C) Effect of LN16026F3 on First Entrance to Target—Probe Trial

Values are expressed as Mean±S.E.M; n=7 animals/group; #$p<0.05$ as compared Scopolamine group (G2) by One-way ANOVA followed by Dunnett's Test.

DETAILED DESCRIPTION OF THE INVENTION

Aging usually accompanies with some degree of decline in cognitive capacity in humans, and if untreated, progresses into more serious conditions, such as dementia and depression, or even Alzheimer's disease. The "cholinergic hypothesis" is well documented in the prior art, which proposes that deficiency of acetylcholine is critical in the genesis of symptoms of degenerative diseases such as age-associated memory impairment and senile dementias.

Acetylcholine is a neurotransmitter. Inside the brain, acetylcholine functions as a neuromodulator and it alters the way other brain structures process information. Acetylcholinesterase is an enzyme which metabolizes acetylcholine in the synaptic cleft. It is thus known in the art that inhibitors of acetylcholinesterase enzyme improve the cognition and alleviate the symptoms of degenerative disorders through enhancing cortical cholinergic neurotransmission. The acetylcholinesterase (AChE) inhibitors increase the concentration of acetylcholine and help nerve cells to communicate better, increase memory, retention and attention. Overall, AChE inhibitors can increase the brain health and function.

Hence, the inventors of the present application randomly screened several ingredients of natural origin and identified a few extracts and fractions with potent Acetylcholinesterase inhibitory activity, which include extracts and fractions of *Bacopa monnieri* and *Terminalia chebula*. The inventors then randomly prepared several compositions with selected ingredients and tested their efficacy in inhibiting acetylcholinesterase enzyme. It was found surprisingly that the compositions comprising extracts or fractions derived from *Bacopa monnieri* in combination with extracts or fractions derived from *Terminalia chebula* showed more potent inhibition of acetylcholinesterase enzyme (Example 6 and Table-1-6), when compared to the efficacy shown by the corresponding individual extracts or fractions derived from *Bacopa monnieri* and *Terminalia chebula*. The acetylcholinesterase inhibitory effects shown by the compositions (LN16026F1, LN16026F2, LN16026F3, LN16026F4 and LN16026F5) containing *Bacopa monnieri* extract (LN17097) standardized to 55% total bacopasides by spectrophotometric assay and *Terminalia chebula* fruit water extract (LN17117 A), for example, are summarized in Table-1 along with and those of their individual ingredients. The *Bacopa monnieri* extract (LN17097) is a bacosides enriched fraction produced by aqueous ethanol extraction followed enrichment through re-extraction using ethanol. This extract contains not less than 55% total bacosides by Spectrometric method of analysis and/or not less than 8% of total bacosides by HPLC method of analysis. The *Bacopa monnieri* extract (LN17097) at 3133 µg/mL and *Terminalia chebula* extract (LN17117 A) at 16.67 µg/mL concentrations showed acetylcholinesterase inhibitions of 17.71% and 9.18% respectively. The composition LN16026F2 containing these two ingredients in 2:1 ratio showed 38.17% inhibition at 50 µg/mL concentration. This observed inhibition (38.17%) is superior than the additive effect (17.71%+9.18%=25.89%) calculated from the inhibitions shown by the individual ingredients. Similarly, the same *Bacopa monnieri* extract at 16.67 µg/mL and *Terminalia chebula* extract at 33.33 µg/mL, concentrations showed acetylcholinesterase inhibitions of 8.36% and 18.35% respectively, whereas the composition LN16026F4 containing these two ingredients in 1:2 ratio showed 36.49% inhibition at 50 µg/mL concentration. This observed inhibition (38.17%) is also better than the additive effect (8.36%+18.35%=26.71%) calculated from the inhibitions shown by the individual ingredients. The other compositions containing these ingredients at other ratios also showed similar improved inhibitory effects as summarized in table-1, when compared to the corresponding individual ingredients. The foregoing data thus suggests that the *Bacopa monnieri* extract (LN17097) standardized to 55% total bacopasides and *Terminalia chebula* fruit water extract (LN17117A) exhibit synergism in acetylcholinesterase enzyme inhibition. The compositions containing 80% ethanol extract of *Bacopa monnieri* (LN17096G), standardized to contain not less than 25% total bacosides by spectroscopic method of analysis and not less than 5% total bacosides by HPLC method of analysis, in combination with water extract of *Terminalia chebula* fruit also showed synergistic inhibition of acetylcholinesterage enzyme as summarized in table-2. The *Bacopa monnieri* extract enriched to not less than 40% of total bacosides (LN17096H) obtained by washing the hydroalcohol extract of *Bacopa monnieri* with water, also showed synergism when combined with *Terminalia chebula* water extract (Table 6). Similarly, alcohol extract (LN17117C) and hydro alcohol extract (LN17117B) of *Terminalia chebula* fruit also showed synergistic inhibition of acetylcholinesterase enzyme when combined with enriched *Bacopa monnieri* extract enriched to contain not less than 55% total bacosides and *Bacopa monnieri* hydroalcoholic extract.

Reactive Oxygen Species (ROS) are formed as a natural byproduct of the normal metabolism of oxygen and have important roles in cell signaling and homeostasis. ROS are known to act as a double-edged sword with respect to memory function. Under physiological conditions, ROS act as essential signaling molecules, necessary for the proper formation of learning and memory processes. However, during aging, ischemia, trauma, or neurodegenerative diseases, the levels of ROS increase to levels higher than the antioxidant machinery of the cells can handle, and therefore their beneficial signaling role becomes outweighed by the ambiance of oxidative damage that they create. Excess generation of ROS has been linked to impaired learning and memory processes, mainly via their toxic effect on the neuronal circuitry necessary for memory formation. In addition, neurodegenerative disorders are characterized by progressive and irreversible loss of neurons from specific regions of the brain. Examples are amyotrophic lateral sclerosis, Parkinson's, Alzheimer's, and Huntington's diseases.

Therefore, the inventors of the present invention further tested the synergistic compositions comprising extracts or fractions derived from *Bacopa monnieri* in combination with extracts or fractions derived from *Terminalia chebula* for their antioxidant potential and surprisingly found that the inventive synergistic compositions showed superior Superoxide Scavenging Activity (NBT assay) (Example 7 and Table-7-10) and superior inhibition of Reactive Oxygen Species (Example 8 and Table-11-16), when compared to the efficacy shown by their individual components.

Figure 1:
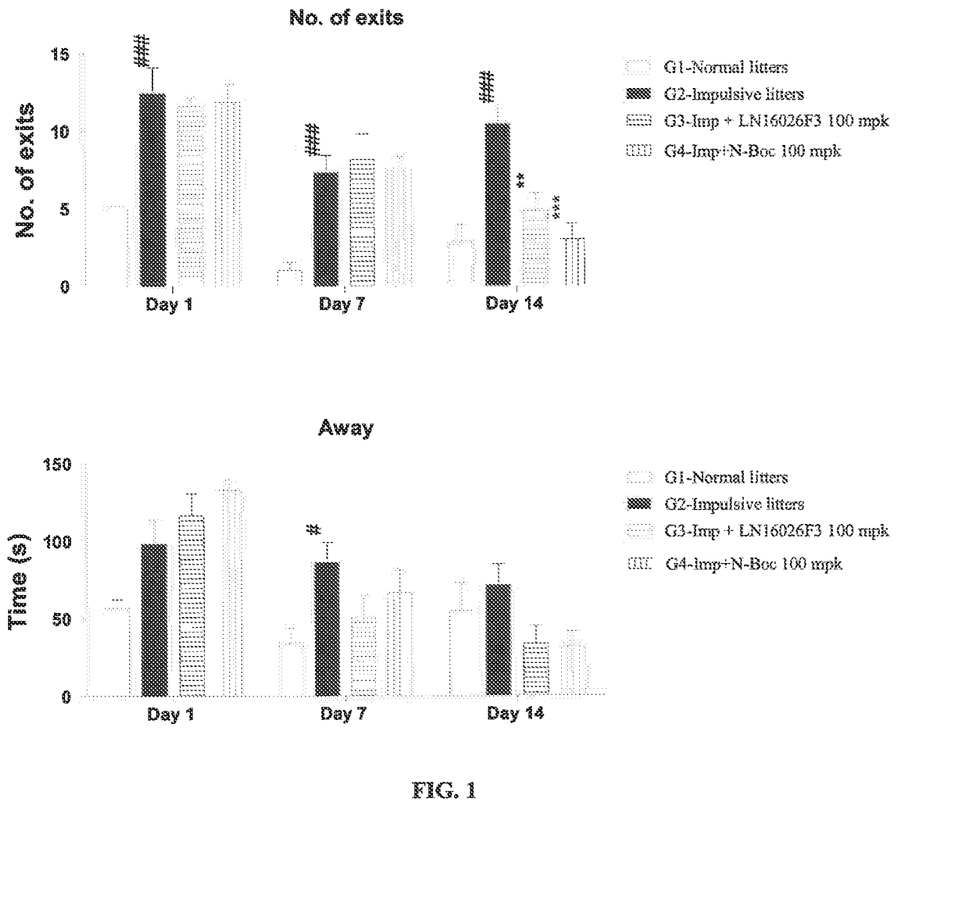
FIG. 1: Modulation of impulsivity behaviors such as number of exits (1A) and time away (1B) from the platform in the treatment groups (G3 and G4) in comparison with the untreated control group (G2).
Figure 2:
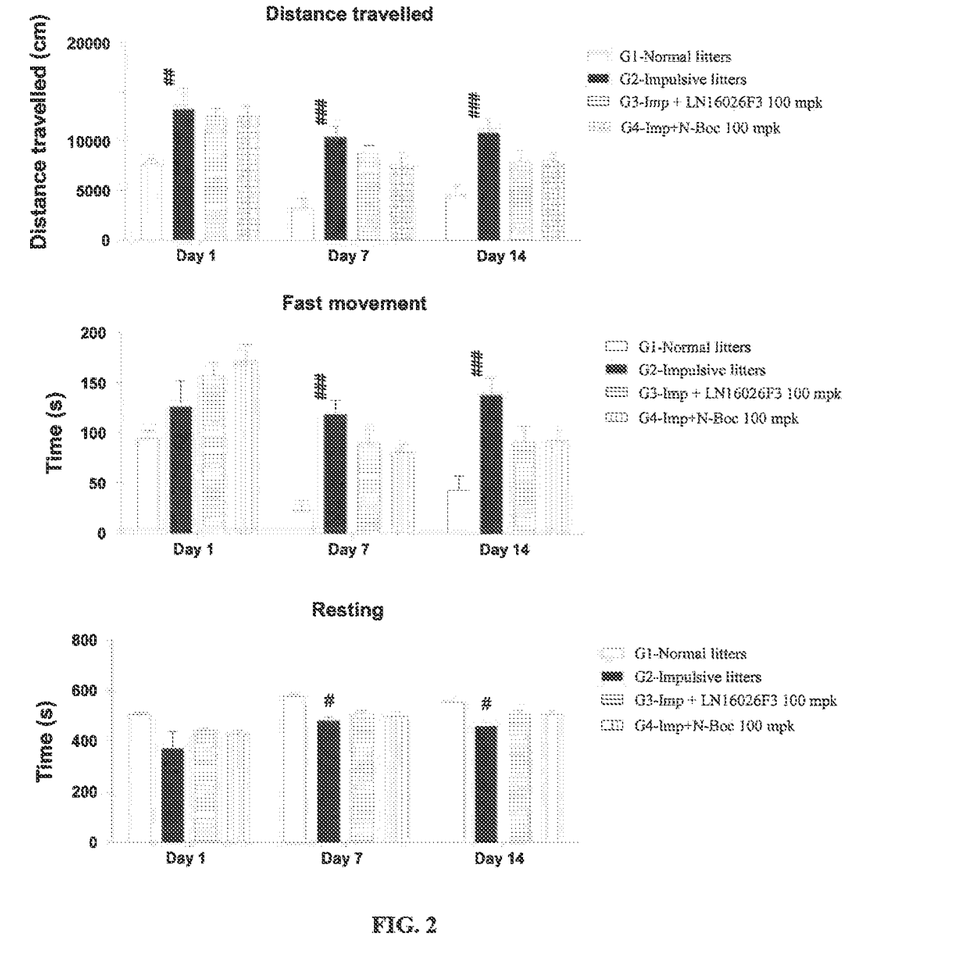
FIG. 2: The efficacy of test substances LN16026F3 (G3) and positive control (G4) in controlling in Locomotor activity in comparison to the controlled group (G2).
Figure 3:
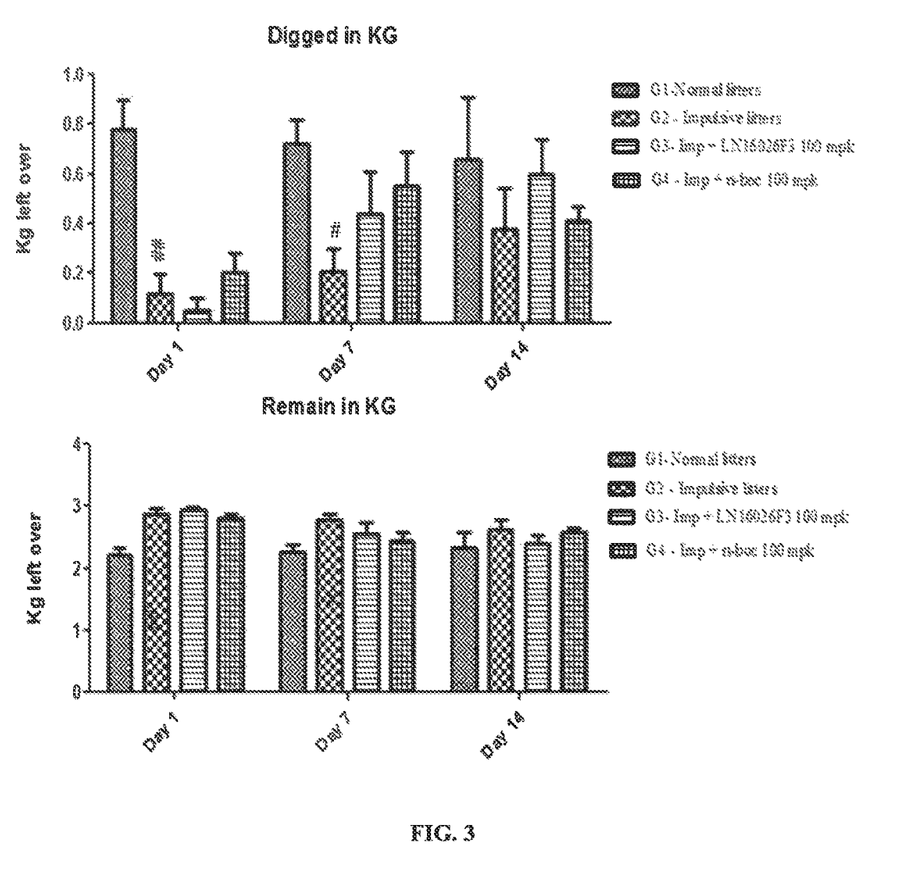
FIG. 3: The efficacy of test substances LN16026F3 (G3) and positive control (G4) in controlling in impulsivity behavior as measured from Burrowing behavior of male litters during treatment period in comparison to the controlled group (G2).

The efficacy shown by the composition in in vitro assays was validated in vivo in Rat model of impulsivity. Impulsivity was induced in male Sprague Dawley rat litters by exposing the pregnant mothers to deltamethrin. The treatment group of animals supplemented with the composition LN16026F3 alleviated the symptoms related to impulsivity behavior, such as behavior in circular tank, locomotor activity and burrowing activity as summarized in example 9 and FIGS. 1 to 3, suggesting its possible use as a therapeutic option for ADHD.

Figure 4:
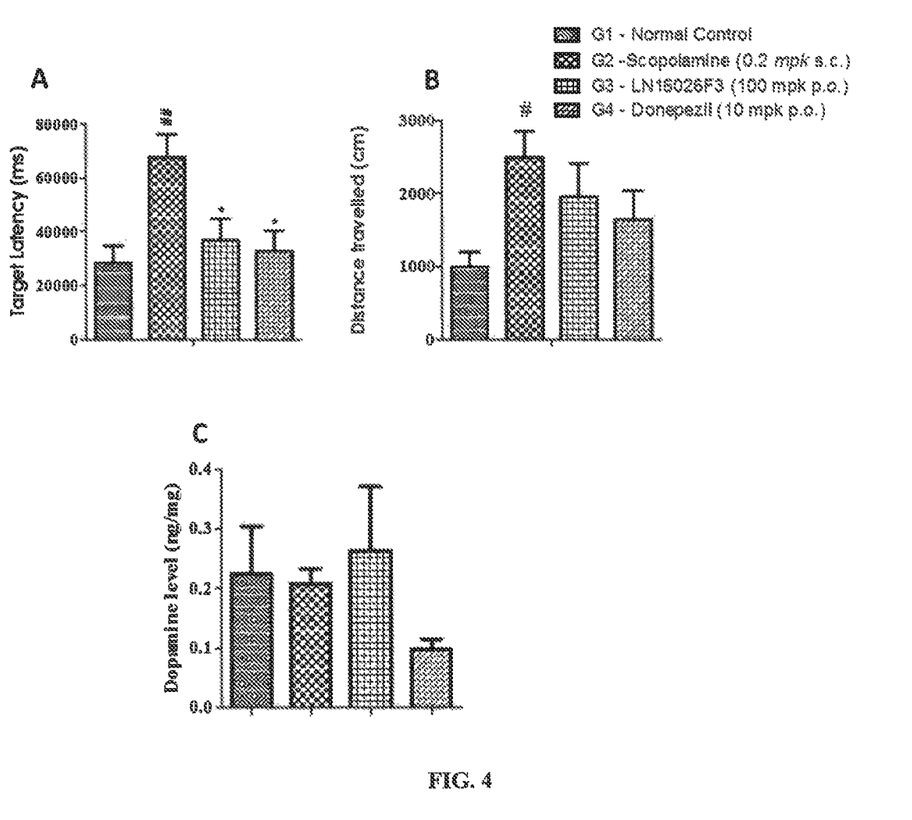
Figure 5:
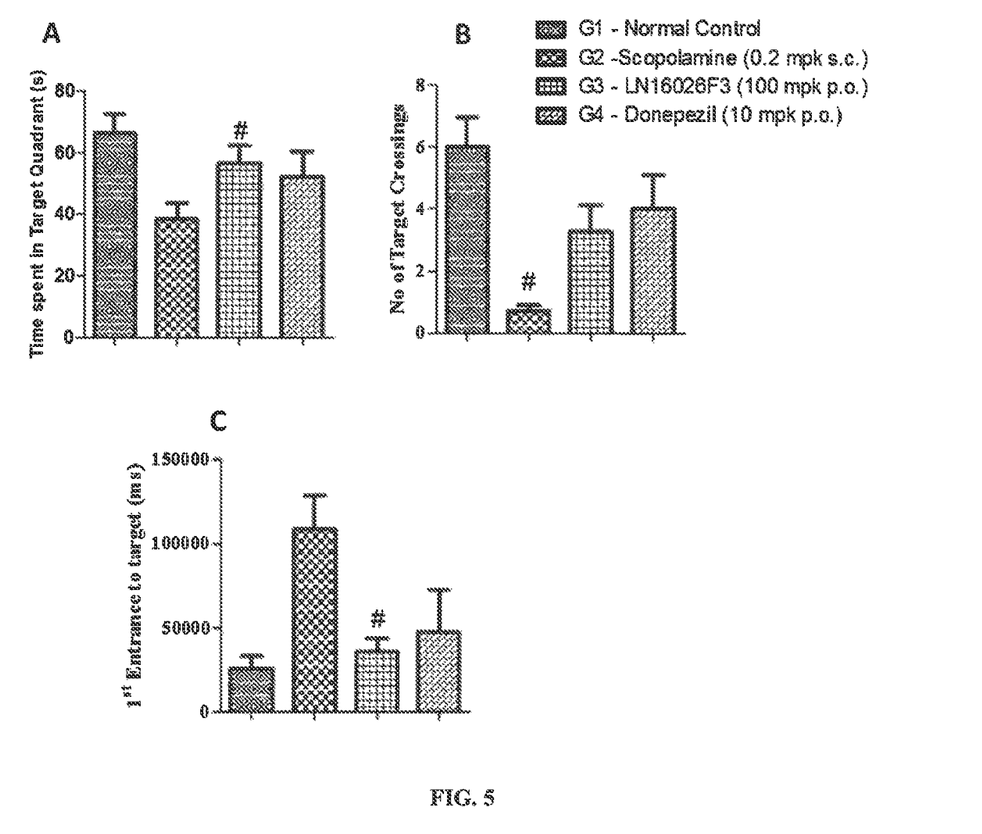
FIG. 5: A) Effect of LN16026F3 on Time spent (ms) in Target Quadrant—Probe Trial Values are expressed as Mean±S.E.M; n=7 animals/group; #$p<0.05$ as compared Scopolamine group (G2) by One-way ANOVA followed by Dunnett's Test.

In a second experiment, the efficacy of the composition LN16026F3 was evaluated memory acquisition and memory recollection in scopolamine induced memory impairment model of Sprague Dawley rats using Morris Water Maze. LN16026F3 significantly improved the learning ability and memory acquisition as indicated by the reduction in target latency and distance travelled as summarized in FIGS. 4A and 4B respectively. Similarly, LN16026F3 also improved the retention of memory as indicated by the reduction in time for reaching the target, increased time spent in the target quadrant, increased number crossings over the target as summarized in FIGS. 5A, 5B and 5C. In addition, the animals treated with LN16026F3 also showed increased levels of dopamine in the brain tissue from the hippocampal region as shown in FIG. 4C

Even though the invention has been demonstrated with selected extracts and plant parts of *Bacopa monnieri* and *Terminalia chebula*, other solvent extracts and other plant parts can also be used for making the synergistic compositions.

Thus, in a preferred embodiment the present invention provides novel synergistic compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula* for improving brain health and brain functions, which include but not limited to cognition, memory, memory retention, memory recollection, intelligence, motivation, attention, concentration, learning power and better communication and to alleviate disease conditions related to cognition and memory deficits and the like.

In another preferred embodiment, the present invention provides synergistic compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula* for enhancing learning and memory, which include but not limited to improved acquisition, improved retention, improved recollection, improved concentration, improved cognitive performance, delayed extinction, mental acuity, and faster reaction, improved memory free recall, improved retention of new information and also decreased the rate of forgetting, improved attention, cognitive processing and working memory.

In other embodiment the present invention provides, novel synergistic compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula* for improving brain health and brain functions, which include but not limited to cognition, memory, memory retention, intelligence, motivation, attention, concentration, wherein, the synergistic compositions may contain optionally pharmaceutically or nutraceutically or dietically acceptable actives, excipients, carriers or diluents, wherein the pharmaceutically or dietetically acceptable excipients, carriers and diluents can be selected from glucose, fructose, sucrose, maltose, yellow dextrin, white dextrin, aerosil, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, proteins, calcium salts, pigments, flavors, preservatives, distilled water, saline, aqueous glucose solution, alcohol, propylene glycol and polyethylene glycol, various animal and vegetable oils, white soft paraffin, paraffin, flavorants, colourants and wax.

In other embodiment, the present invention provides novel synergistic compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula*, wherein the compositions may be formulated into a dosage form selected from dry powder form, liquid form, beverage, food product, dietary supplement or any suitable form such as tablet, a capsule or a soft chewable or gummy bear.

In yet another embodiment, the present invention provides novel synergistic compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula*, wherein the composition(s) can be made into the dosage form of healthy foods, or food for specified health uses such as solid food like chocolate or nutritional bars, semisolid food like cream or jam, or gel and also beverage and the like, such as refreshing beverage, lactic acid bacteria beverage, drop, candy, chewing gum, gummy candy, yoghurt, ice cream, pudding, soft adzuki bean jelly, jelly, cookie, tea, soft drink, juice, milk, coffee, cereal, snack bar and the like.

In another embodiment, the invention provides use of synergistic compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula* for improving brain health and brain functions, to prevent, control and treat brain related diseases/disorders which include but not limited to senile dementia, multi-infarct dementia, dyslexia, aphasia, organic brain syndrome, myasthenia gravis, vascular dementia, mild cognitive impairment (MCI), Lewy body dementia, Wemicke-Korsakoff-syndrome, Alzheimer's disease, Parkinson's disease, Attention-deficit Hyperactivity Disorder (ADHD), hypoxia, anoxia, cerebrovascular insufficiency, epilepsy, myoclonus and hypo cholinergic dysfunctions, to slowdown memory deterioration, functional loss and to treat memory impairment disorders, neurodegenerative disorders and for controlling blood pressure and blood circulation in the brain.

In further embodiment, the invention provides compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula* for improving brain health and brain functions, wherein the compositions further containing optionally at least one component selected from biological agent(s), antioxidants, anti-inflammatory agents, immune modulators and Nootropic agent(s).

In other important embodiment, the present invention provides method of improving brain health and brain functions, which include but not limited to cognition, memory, memory retention, intelligence, motivation, attention, concentration, learning power and communication and to alleviate disease conditions related to cognition and memory deficits and the like in a mammal, wherein the method comprises supplementing the mammal with an effective dose of the synergistic composition comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula* optionally containing at least one ingredient selected from pharmaceutically or nutraceutically or dietically acceptable actives, excipients, carriers or diluents.

In other important embodiment, the present invention provides method of improving learning and memory, which include but not limited to improving acquisition, improving retention, improving concentration, improving memory recollection, improving cognitive performance; delayed extinction, mental acuity, and faster reaction; improving memory free recall and retention of new information; and also decreased the rate of forgetting, improved attention, cognitive processing, and working memory, wherein the method comprises supplementing the mammal with an effective dose of the synergistic composition comprising at least one extract or fraction derived from *Bacopa monnieri* in combination with at least one extract or fraction derived from *Terminalia chebula* optionally containing at least one ingredient selected from pharmaceutically or nutraceutically or dietically acceptable actives, excipients, carriers or diluents.

In another embodiment, the invention provides methods of use of synergistic compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula* to prevent, control and treat brain related diseases/disorders which include but not limited to senile dementia, multi-infarct dementia, dyslexia, aphasia, organic brain syndrome, myasthenia gravis, vascular dementia, mild cognitive impairment (MCI), Lewy body dementia, Wernicke-Korsakoff-syndrome, Alzheimer's disease, Parkinson's disease, Attention-deficit Hyperactivity Disorder (ADHD), hypoxia, anoxia, cerebrovascular insufficiency, epilepsy, myoclonus and hypo cholinergic dysfunctions, to slowdown memory deterioration, functional loss and to treat memory impairment disorders, neurodegenerative disorders, and for controlling blood pressure and blood circulation in the brain.

In another embodiment, the invention provides methods of use of synergistic compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula* for improving learning and memory, which include but not limited to improving acquisition, improving retention, improving concentration, improving memory recollection, improving cognitive performance; delayed extinction, mental acuity, and faster reaction; improving memory free recall and retention of new information; and also decreased the rate of forgetting, improved attention, cognitive processing, and working memory, wherein the method comprises supplementing the mammal with an effective dose of the synergistic composition optionally containing at least one ingredient selected from pharmaceutically or nutraceutically or dietically acceptable actives, excipients, carriers or diluents.

In another embodiment, the invention provides synergistic compositions comprising at least one component selected from extract(s), fraction(s), active compound(s) and phytochemicals or mixtures thereof derived from *Bacopa monnieri* in combination with at least one component selected from extract(s), fraction(s), active compound(s) and phytochemicals or mixtures thereof derived from *Terminalia chebula* for improving brain health and brain functions, wherein, the plant parts used in the present invention for the preparation of synergistic composition are fruits in case of *Terminalia chebula* extract and whole plant, aerial parts or leaves in case of *Bacopa monnieri* extract.

In other embodiment, the invention provides synergistic compositions comprising at least one component selected from extract(s), fraction(s), active compound(s) and phytochemicals or mixtures thereof derived from *Bacopa monn-*

*ieri* in combination with at least one component selected from extract(s), fraction(s), active compound(s) and phytochemicals or mixtures thereof derived from *Terminalia chebula* for improving brain health and brain functions, wherein solvents used for preparing the extracts and fractions can be selected from but not limited to C1-05 alcohols, like ethanol, methanol, n-propanol, isopropyl alcohol; ketones like acetone, methylisobutyl ketone, chlorinated solvents like methylene dichloride and chloroform, water and mixtures thereof; C1-C7 hydrocarbons such as hexane; esters like ethyl acetate and the like and mixtures thereof.

In yet another embodiment, the invention provides synergistic compositions comprising at least one extract or fraction derived from *Bacopa monnieri* in combination with at least one extract or fraction derived from *Terminalia chebula* for improving brain health and brain functions, wherein, the weight of *Bacopa monnieri* extract in the composition varies in the range of 20%-80% and the weight of *Terminalia chebula* extract varies in the range of 80%-20%.

In other embodiment, the invention provides synergistic compositions comprising at least one extract or fraction derived from *Bacopa monnieri* in combination with at least one extract or fraction derived from *Terminalia chebula* for improving brain health and brain functions, wherein, the *Bacopa monnieri* extract or fraction contains total bacosides in the range of 20 to 70% as per spectrometric method of analysis and/or 5 to 25% of total bacosides as per HPLC method of analysis.

In other embodiment, the invention provides synergistic compositions comprising at least one extract or fraction derived from *Bacopa monnieri* in combination with at least one extract or fraction derived from *Terminalia chebula* for improving brain health and brain functions, wherein, the *Terminalia chebula* extract or fraction contains total polyphenols in the range of 20 to 80% as per spectrometric method of analysis, 1 to 6% total chebulagic acids and 1-12% total chebulinic acid as per HPLC method of analysis, 1 to 10% ellagic acid and/or 1 to 10% gallic acid. The following examples, which include preferred embodiments, will serve to illustrate the practice of this invention, it being understood that the particulars shown are by way of example and for purpose of illustrative discussion of preferred embodiments of the invention.

Example 1

Preparation of *Bacopa monnieri* Aqueous Ethanol Extract 25% (LN17096 G), *Bacopa monnieri* Extract 40% Total Bacosides (LN 17096 H) and *Bacopa monnieri* Extract 55% Total Bacosides (LN 17097):

Dried plant material of *Bacopa monnieri* aerial parts (1 Kg) was pulverized to coarse powder and extracted with 80% aqueous alcohol (8 L) for 2 hrs at reflux temp. The extract was separated from the raw material residue by filtration and the extraction process was repeated twice on the residue using 5 L of 80% alcohol each time. The extracts were combined and the solution was subjected to fine filtration. The filtrate was concentrated under reduced pressure to give a residue (225-240 g; LN17096G). The extract showed not less than 25% total bacosides by UV method of analysis and not less than 5% total bacosides (bacopaside I, bacoside A3, bacopaside II, bacoside X and bacopasaponin C) by HPLC method of analysis.

To the above crude 80% alcoholic extract (LN17096 G; 100 g) was added RO water (400 mL) and the solution was subjected to vigorous stirring. The mixture was filtered and the solid compound was dried in vacuum dryer to obtain *Bacopa monnieri* extract powder (LN 17096H) containing not less than 40% total bacosides by UV method of analysis and not less than 10% of total bacosides by HPLC method of analysis The above crude 80% alcoholic extract (LN17096 G; 200 g) was subjected to re-extraction with 400 mL of commercial ethyl alcohol at room temperature for two hours. The extract was separated from the residue by filtration. The residue was re-extracted under similar conditions. The extracts were combined, fine filtered and the solution concentrated under reduced pressure followed by vacuum drying to obtain *Bacopa* extract powder (LN 17097; 75-85 g). The extract contains not less than 55% total bacopasides by Spectrophotometric method of analysis and not less than 8% total bacosides (bacopaside I, bacoside A3, bacopaside II, bacoside X and bacopasaponin C) by HPLC method of analysis.

Example 2

Preparation of *Terminalia chebula* Water Extract (LN17117A).

Dried fruit plant material of *Terminalia chebula* (1 Kg) was pulverized to coarse powder and extracted with water (6 L) at 65-70° C. for 2 hr. The extract was separated from the raw material by filtration. Extraction process was repeated twice on the raw material residue under similar extraction conditions. All the extracts were combined, the combined extract was fine filtered, and the clear extract was evaporated to dryness on a climbing film evaporator at 50-60° C. to obtain extract concentrate, which was then subjected to final drying in a vacuum dryer to obtain *Terminalia chebula* water extract (LN17117A) as a powder (370 g). The extract contains not less than 65% polyphonols as per spectrometric method of analysis and 6% total chebulagic acids, 12% total chebulinic acid 4% ellagic acid and/or 8% gallic acid as per HPLC method of analysis.

Example 3

Preparation of *Terminalia chebula* 50% ethanol extracts (LN17117B):

Dried fruits of the plant material *Terminalia chebula* (500 g) were pulverized to coarse powder and extracted with 50% ethanol (5 L) at 65-70° C. for 2 hr. The extract was separated from the raw material by filtration. Extraction process was repeated twice on the raw material residue under similar extraction conditions using 3 L of 50% ethanol each time. All the extracts were combined, the combined extract was fine filtered, and the clear extract was evaporated to dryness on a climbing film evaporator at 50-60° C. to obtain extract concentrate, which was then subjected to final drying in a vacuum dryer to obtain *Terminalia chebula* aqueous alcohol extract (LN 17117B) as a powder (234 g). The extract contains not less than 60% polyphonols as per spectrometric method of analysis and 4% total chebulagic acids, 8% total chebulinic acid 3% ellagic acid and/or 6% gallic acid as per HPLC method of analysis.

Example 4

Preparation of *Terminalia chebula* ethanol extract (LN17117C):

Dried fruit plant material of *Terminalia chebula* (500 g) was pulverized to coarse powder and extracted with ethanol (5 L) at reflux temperature for 2 hr. The extract was separated from the raw material by filtration. Extraction process was repeated twice on the raw material residue under similar extraction conditions using 3 L of 50% ethanol each time. All the extracts were combined, the combined extract was fine filtered, and the clear extract was evaporated to dryness on a climbing film evaporator at 50-60° C. to obtain extract concentrate, which was then subjected to final drying in a vacuum dryer to obtain *Terminalia chebula* alcohol extract (LN17117C) as a powder (245 g).

Example 5

Preparation of Compositions Containing *Bacopa monnieri* Extracts and *Terminalia chebula* Extracts Composition-1: composition-1 (LN16026F1) was prepared by mixing *Bacopa monnieri* 55% extract (LN 17097) and *Terminalia chebula* water extract (LN17117A) in a 3:1 ratio.

Composition-2: composition-2 (LN16026F2) was prepared by mixing *Bacopa monnieri* 55% extract (LN17097) and *Terminalia chebula* water extract (LN17117A) in the ratio of 2:1.

Composition-3: composition-3 (LN16026F3) was prepared by mixing *Bacopa monnieri* 55% extract (LN17097) and *Terminalia chebula* water extract (LN17117A) in the ratio of 1:1.

Composition-4: composition-4 (LN16026F4) was prepared by mixing *Bacopa monnieri* 55% extract (LN17097) and *Terminalia chebula* water extract (LN17117A) in the ratio of 1:2.

Composition-5: composition-5 (LN16026F5) was prepared by mixing *Bacopa monnieri* 55% extract (LN17097) and *Terminalia chebula* water extract (LN17117A) in the ratio of 1:3.

Composition-6: Composition-6 (LN17118A) was prepared by mixing *Bacopa monnieri* 55% extract (LN17097) and *Terminalia chebula* ethanol extract (LN17117C) in the ratio of 1:1.

Composition-7: Composition-7 (LN17118B) is prepared by mixing *Bacopa monnieri* 55% extract (LN17097) and *Terminalia chebula* hydro alcohol extract (LN17117B) in the ratio of 1:1.

Composition-8: Composition-8 (LN17119A) is prepared by mixing *Bacopa monnieri* 80% alcohol extract 25% bacosides (LN17096G) and *Terminalia chebula* water extract LN 17117A in the ratio of 1:1.

Composition-9: Composition-9 (LN17119C) is prepared by mixing *Bacopa monnieri* 80% alcohol extract 25% bacosides (LN17096G) and *Terminalia chebula* ethanol extract (LN17117C) in the ratio of 1:1.

Composition-10: Composition-10 (LN17119B) is prepared by mixing *Bacopa monnieri* 80% alcohol extract 25% bacosides (LN17096G) and *Terminalia chebula* hydro alcohol extract (LN17117B) in the ratio of 1:1.

Composition-11:—Composition-11 (LN17120) is prepared by mixing *Bacopa monnieri* extract 40% bacosides (LN 17096H) and *Terminalia chebula* hydro alcohol extract (LN17117B) in the ratio of 1:1.

Example 6

Efficacy of *Bacopa monnieri* Extracts and *Terminalia chebula* Water Extracts and their Compositions in Inhibition of Acetyl Cholinesterase:

Acetylcholinesterase activity was measured using the substrate acetylthiocholine iodide, which converts to thiocholine. The reaction of thiocholine with the chromogenic substrate Dithionitrobenzoic acid (DTNB) leads to the formation of a yellow anion of 2-thio-2-Nitrobenzoic acid, which absorbs strongly at 412 nm. Incubation was done for 10 min The AChE assay was performed by the method of Ellman et. al, with minor modifications, using acetylthiocholine iodide as a substrate (Lee J. H., et. al. Arch Pharm Res 2004, 27(1): 53-56). Ellmans reaction mixture contains 0.5 mM acetylthiocholine iodide and 1 mM 5,5'-dithio-bis-(2-nitrobenzoic acid) in a 50 mM sodium phosphate buffer (pH 8.0). The assay mixture contained 50 µl of 50 mM phosphate buffer at pH—8.0, 30 µl of test substance at various concentrations and 20 µl of (100 mU/mL) enzyme. For blanks, the enzyme was replaced with phosphate buffer. The reaction mixture was mixed thoroughly, 100 µl of Ellman's reagent was added and incubated at room temperature for 10 min. The absorbance was measured at 412 nm using microplate reader. The percentage inhibition of enzyme activity was calculated by comparing OD's of tests wells with that of control wells using the following formula. Calculations: % inhibition=[(control-sample)/control]×100. The results of Acetylcholinesterase inhibitory activity of the individual extracts of *Bacopa monnieri* and *Terminalia chebula* and their synergistic compositions are summarized in Tables 1-6.

TABLE 1

| Composition # | LN 17097 | | LN17117A | | Ratio | % inhibition Additive (calculated) | % inhibition Observed at 50 µg |
|---|---|---|---|---|---|---|---|
| | µg/mL | % inhibition | µg/mL | % inhibition | | | |
| LN16026F1 | 37.5 | 18.80 | 12.50 | 6.88 | 3:1 | 25.69 | 32.22 |
| LN16026F2 | 33.33 | 16.71 | 16.67 | 9.18 | 2:1 | 25.89 | 38.17 |
| LN16026F3 | 25.00 | 12.54 | 25.00 | 13.77 | 1:1 | 26.30 | 40.44 |
| LN16026F4 | 16.67 | 8.36 | 33.33 | 18.35 | 1:2 | 26.71 | 36.49 |
| LN16026F5 | 12.50 | 6.27 | 37.50 | 20.65 | 1:3 | 26.92 | 35.85 |

In Table 2:
- LN17096G is: *Bacopa monnieri* aqueous ethanol extract;
- LN17117A is: *Terminalia chebula* water extract; and
- LN17119A is: LN17096G and LN 17117A in a ratio of 1:1.

TABLE 2

| Comp | Comp dose µg/ml | LN17096 G µg/ml | LN17096 G % inhibition | LN17117A µg/ml | LN17117A % inhibition | Ratio | % inhibition of Ache Additive (Calculated) | % inhibition of Ache Observed |
|---|---|---|---|---|---|---|---|---|
| LN17119A | 12.5 | 6.25 | 5.40 | 6.25 | 1.82 | 1:1 | 7.22 | 14.22 |

In Table 3:
- LN17097 is: *Bacopa monnieri* extract 55% total bacosides;
- LN17117C is: *Terminalia chebula* ethanol extract; and
- LN17118A is: LN17097 and LN17117C in a ratio of 1:1.

TABLE 3

| Comp | Comp dose µg/ml | LN 17097 µg/ml | LN 17097 % inhibition | LN17117C µg/ml | LN17117C % inhibition | Ratio | % inhibition of Ache Additive (Calculated) | % inhibition of Ache Observed |
|---|---|---|---|---|---|---|---|---|
| LN17118 A | 6.25 | 3.125 | 4.7 | 3.125 | 5.04 | 1:1 | 9.74 | 16.16 |
|  | 12.5 | 6.25 | 8.43 | 6.25 | 1.50 |  | 9.93 | 15.15 |
|  | 25 | 12.5 | 12.23 | 12.5 | 10.97 |  | 23.2 | 26.52 |
|  | 50 | 25 | 17.58 | 25 | 15.04 |  | 32.62 | 34.09 |

In Table 4:
- LN17097 is: *Bacopa monnieri* extract 55% total bacosides;
- LN17117B is: *Terminalia chebula* 50% ethanol extract; and
- LN17118B is: LN17097 and LN17117B in a ratio of 1:1.

TABLE 4

| Comp | Comp dose µg/ml | LN 17097 µg/ml | LN 17097 % inhibition | LN17117B µg/ml | LN17117B % inhibition | Ratio | % inhibition of Ache Additive (Calculated) | % inhibition of Ache Observed |
|---|---|---|---|---|---|---|---|---|
| LN17118B | 100 | 50 | 12.88 | 50 | 16.14 | 1:1 | 29.02 | 44.02 |

In Table 5:
- LN17096G is: *Bacopa monnieri* aqueous ethanol extract;
- LN17117C is: *Terminalia chebula* ethanol extract; and
- LN17119C is: LN17096G and LN17117C in a ratio of 1:1.

TABLE 5

| Comp | Comp dose µg/ml | LN17096 G µg/ml | LN17096 G % inhibition | LN17117C µg/ml | LN17117C % inhibition | Ratio | % inhibition of Ache Additive (Calculated) | % inhibition of Ache Observed |
|---|---|---|---|---|---|---|---|---|
| LN17119C | 12.5 | 6.25 | 5.40 | 6.25 | 1.50 | 1:1 | 6.9 | 23.66 |
|  | 25 | 12.5 | 8.98 | 12.5 | 10.97 |  | 19.95 | 24.19 |

In Table 6:
  LN17096H is: *Bacopa monnieri* extract 40% total bacosides;
  LN17117B is: *Terminalia chebula* 50% ethanol extract; and
  LN17120 is: LN17096G and LN17117C in a ratio of 1:1.

TABLE 6

| Comp | Comp dose µg/ml | LN 17096H µg/ml | LN 17096H % inhibition | LN17117B µg/ml | LN17117B % inhibition | Ratio | % inhibition of Ache Additive (Calculated) | % inhibition of Ache Observed |
|---|---|---|---|---|---|---|---|---|
| LN17120 | 25 | 12.5 | 13.51 | 12.5 | 5.95 | 1:1 | 19.46 | 38.93 |

Example-7

Efficacy of *Bacopa monnieri* Extracts and *Terminalia chebula* Extracts and their Compositions in Superoxide Scavenging Activity (NBT Assay):

Superoxide radical scavenging activity of test compounds was determined spectrophotometrically (560 nm) by following the nitro blue tetrazolium (NBT) photo reduction method of McCord and Fridovich (Mc Cord and Fridovich, I. (1969) Superoxide dismutase on enzymatic function for erythrocumein. J. Biol. Chem. 24, 6049-6055) the assay mixture contained EDTA (6.6 µM), NaCN (3 µg), riboflavin (2 µM), NBT (50 µM), test substance and phosphate buffer (58 mmol, pH 7.8) in a final volume of 3 mL. Each mixture in a tube was shaken well, and the optical density was measured at 560 nm. Each tube was then uniformly illuminated with an incandescent lamp for 15 min, and the optical density was measured again at 560 nm. The percentage inhibition of superoxide radical-generation was measured by comparing the absorbance values of the control and that of the test substance. The $IC_{50}$ values were obtained from a plot drawn between concentrations (µM) versus the percentage inhibition. The super-oxide radical's inhibitions exhibited by individual compounds and their compositions have been summarized in Tables 7-10.

TABLE 7

Superoxide Scavenging Activity (NBT assay)

| Composition # | LN 17097 µg/mL | LN 17097 % inhibition | LN17117 A µg/mL | LN17117 A % inhibition | Ratio | % inhibition Additive (calculated) | % inhibition Observed at 100 µg |
|---|---|---|---|---|---|---|---|
| LN16026F1 | 75.00 | 47.68 | 25.00 | 22.61 | 3:1 | 70.28 | 87.68 |
| LN16026F2 | 66.66 | 42.38 | 33.33 | 30.14 | 2:1 | 72.52 | 90.43 |
| LN16026F3 | 50.00 | 31.79 | 50.00 | 45.21 | 1:1 | 77.00 | 93.07 |
| LN16026F4 | 33.33 | 21.19 | 66.66 | 60.28 | 1:2 | 81.47 | 94.49 |
| LN16026F5 | 25.00 | 15.89 | 75.00 | 67.82 | 1:3 | 83.71 | 94.07 |

In Tables 8-10:
  LN 17097 is: *Bacopa monnieri* extract 55% total bacosides;
  LN17096G is: *Bacopa monnieri* aqueous ethanol extract;
  LN17117C is: *Terminalia chebula* ethanol extract; and
  LN17117A is: *Terminalia chebula* water extract.

TABLE 8

| Comp | Comp dose µg/ml | LN 17097 µg/ml | % inhibition | LN17117 C µg/ml | % inhibition | Ratio | % inhibition of superoxide Additive (Calculated) | Observed |
|---|---|---|---|---|---|---|---|---|
| LN17118 A | 3.12 | 1.56 | 3.58 | 1.56 | 28.94 | 1:1 | 32.52 | 47.38 |
|  | 6.25 | 3.125 | 8.83 | 3.125 | 39.42 |  | 48.25 | 70.89 |
|  | 12.5 | 6.25 | 16.37 | 6.25 | 43.79 |  | 60.16 | 88.16 |
|  | 25 | 12.5 | 28.95 | 12.5 | 48.5 |  | 77.45 | 92.50 |

TABLE 9

| Comp | Comp dose µg/ml | LN17096 G µg/ml | % inhibition | LN17117 A µg/ml | % inhibition | Ratio | % inhibition of superoxide Additive (Calculated) | Observed |
|---|---|---|---|---|---|---|---|---|
| LN17119 A | 6.25 | 3.125 | 3.64 | 3.125 | 33.88 | 1:1 | 37.52 | 72.08 |
|  | 12.5 | 6.25 | 13.87 | 6.25 | 41.41 |  | 55.28 | 86.89 |
|  | 25 | 12.5 | 29.78 | 12.5 | 45.21 |  | 74.99 | 92.50 |

TABLE 10

| Comp | Comp dose µg/ml | LN17096 G µg/ml | % inhibition | LN17117 C µg/ml | % inhibition | Ratio | % inhibition of superoxide Additive (Calculated) | Observed |
|---|---|---|---|---|---|---|---|---|
| LN17119 C | 6.25 | 3.125 | 3.64 | 3.125 | 39.42 | 1:1 | 43.06 | 58.76 |
|  | 12.5 | 6.25 | 13.87 | 6.25 | 43.79 |  | 57.66 | 76.16 |
|  | 25 | 12.5 | 29.78 | 12.5 | 48.5 |  | 78.28 | 84.66 |

Example-8

Efficacy of *Bacopa monnieri* Extracts and *Terminalia chebula* Extracts and their Compositions in Inhibition of ROS Production:

Anti-oxidant activity of the test sample was evaluated by measuring reactive oxygen species (ROS) scavenging activity in Phorbol 12-myristate 13-acetate (PMA) induced HL-60 human promyelocytes. Briefly, HL-60 cells were washed twice with HBSS and equal number of cells (125000 cells in 50 µl HBSS) was plated in each well of a 96 well plate and 5 µM of a fluorescent dye 2, 7-dichlorofluorescein diacetate (DCFH-DA) was added to each well and incubated for 20 min. The cells were treated with different concentrations of the test sample in presence or absence of 100 nM PMA for up to 2h at 37° C. and the fluorescence was measured at an interval of 10 min (excitation wavelength 460 nm, emission wavelength 550 nm) in a multimode reader (SpectraMax MS, Molecular Devices, Sunnyvale, Calif., USA). The percentages of inhibition of ROS generation by different doses of the test sample were calculated from the AUCs (area under the curve) obtained from the dose response curves. The ROS production inhibitions exhibited by individual compounds and their compositions have been summarized in Tables 11-16.

TABLE 11

Inhibition of ROS production
Test Composition

| LN 17097 (*Bacopa monnieri* extract 55% total bacosides) | | LN17117A (*Terminalia chebula* water extract) | | Mixture of LN17097 and LN17117A (2.5 µg/mL) | | |
|---|---|---|---|---|---|---|
| | | | | Ratio of LN17097: | % inhibition | Expected % inhibition based on additive results |
| µg/mL | % inhibition | µg/mL | % inhibition | LN17117A | (observed) | (calculated) |
| 1.88 | 17.10 | 0.63 | 14.78 | 3:1 | 49.69 | 31.89 |
| 1.67 | 15.21 | 0.83 | 19.70 | 2:1 | 66.83 | 34.91 |
| 1.25 | 11.40 | 1.25 | 29.55 | 1:1 | 59.13 | 40.96 |
| 0.83 | 7.60 | 1.67 | 39.40 | 1:2 | 67.46 | 47.01 |
| 0.63 | 5.70 | 1.88 | 44.33 | 1:3 | 62.62 | 50.03 |

In Tables 12-16:
  LN 17097 is: *Bacopa monnieri* extract 55% total bacosides;
  LN17096G is: *Bacopa monnieri* aqueous ethanol extract;
  LN17117C is: *Terminalia chebula* ethanol extract;
  LN17117B is: *Terminalia chebula* 50% ethanol extract; and
  LN17117A is: *Terminalia chebula* water extract.

TABLE 12

| Comp | Comp dose µg/ml | LN 17097 | | LN17117 C | | Ratio | % inhibition of ROS | |
|---|---|---|---|---|---|---|---|---|
| | | µg/ml | % inhibition | µg/ml | % inhibition | | Additive (Calculated) | Observed |
| LN17118 A | 1 | 0.5 | 1.32 | 0.5 | 30.20 | 1:1 | 31.52 | 54.8 |
| | 2.5 | 1.25 | 12.39 | 1.25 | 31.19 | | 43.58 | 60.99 |
| | 5 | 2.5 | 20.94 | 2.5 | 31.46 | | 52.4 | 62.29 |

TABLE 13

| Comp | Comp dose µg/ml | LN 17097 | | LN17117 B | | Ratio | % inhibition of ROS | |
|---|---|---|---|---|---|---|---|---|
| | | µg/ml | % inhibition | µg/ml | % inhibition | | Additive (Calculated) | Observed |
| LN17118 B | 1 | 0.5 | 1.32 | 0.5 | 29.03 | 1:1 | 30.35 | 52.07 |
| | 2.5 | 1.25 | 12.39 | 1.25 | 30.63 | | 43.02 | 58.34 |
| | 5 | 2.5 | 20.94 | 2.5 | 30.68 | | 51.62 | 60.47 |

TABLE 14

| Comp | Comp dose µg/ml | LN17096 G | | LN17117 A | | Ratio | % inhibition of ROS | |
|---|---|---|---|---|---|---|---|---|
| | | µg/ml | % inhibition | µg/ml | % inhibition | | Additive (Calculated) | Observed |
| LN17119 A | 1 | 0.5 | −3.53 | 0.5 | 28.24 | 1:1 | 24.71 | 57.04 |
| | 2.5 | 1.25 | 17.56 | 1.25 | 35.41 | | 52.97 | 66.99 |
| | 5 | 2.5 | 21.02 | 2.5 | 32.84 | | 53.86 | 73.6 |

TABLE 15

| Comp | | LN17096 G | | LN17117 C | | % inhibition of ROS | |
|---|---|---|---|---|---|---|---|
| Comp | dose µg/ml | µg/ml | % inhibition | µg/ml | % inhibition | Ratio | Additive (Calculated) | Observed |
| LN17119 C | 1 | 0.5 | −3.53 | 0.5 | 30.20 | 1:1 | 26.67 | 57.06 |
| | 2.5 | 1.25 | 17.56 | 1.25 | 31.19 | | 48.75 | 66.17 |
| | 5 | 2.5 | 21.02 | 2.5 | 31.46 | | 52.48 | 72.58 |

TABLE 16

| Comp | | LN17096 G | | LN17117 B | | % inhibition of ROS | |
|---|---|---|---|---|---|---|---|
| Comp | dose µg/ml | µg/ml | % inhibition | µg/ml | % inhibition | Ratio | Additive (Calculated) | Observed |
| LN17119 B | 1 | 0.5 | −3.53 | 0.5 | 29.03 | 1:1 | 25.5 | 53.5 |
| | 2.5 | 1.25 | 17.56 | 1.25 | 30.63 | | 48.19 | 61.9 |
| | 5 | 2.5 | 21.02 | 2.5 | 30.68 | | 51.7 | 68.45 |

Example-9

Investigation of the Effect of LN16026F3 on Impulsivity Using Circular Tank, Burrowing Behavior and Locomotor Activity in Sprague Dawley Rats.

The present study was carried out to investigate the effect of LN16026F3 on Impulsivity using circular tank, burrowing behavior and locomotor activity in Sprague Dawley rats. The procedure involves the induction of impulsivity in male litters in utero by feeding the pregnant mothers with 3 mg/kg body weight of deltamethrin mixed in feed during gestation and lactation periods. Male pups were tested for impulsivity behavior and impulsive animals were randomized into 3 groups of 7 animals each: Group G2 was left untreated; G3 and G4 were treated with LN16026F1 and positive control N-butyloxycarbonyl pyrrolidine (N-Boc Pyrrolidine) respectively for 2 week from the day of weaning, i.e., day 23 of their age. Litters of normal pregnant rats served as normal control (G1). G4 was considered the standard treatment to treat impulsivity.

Circular water tank contains a platform with arms in the center of the tank above the water level. The tank contains four narrow radial lines (arms) extend from this platform. Animals were individually placed on the platform, which is relatively more secure than the narrow lines because it offers less risk of falling in the water. The number of exits and the time spend away from the platform were measured for 5 min. Animals of impulsive group exited more times from platform and exit count of this group is significantly higher over normal control. The animals treated with LN16026F1 exhibited statistically significant reduction in exit count over impulsive control group on day 14. Time spent away from the platform was markedly higher in impulsive group animals in comparison with normal litters on day 1, 7. Treatment with LN1602761 could increase the time taken for first exit. The animals treated with LN16026F1 exhibited reduction in time spent away from platform over impulsive control group on days 7 and day 14. The data is summarized in FIG. 1. Locomotor activity was captured and quantified by tracking the movement of animals in the open field of a large box with SMART video tracking system (PanLab S.L.U) and Locomotor activity is measured in three categories—distance travelled (cm), fast moving time (s) and resting time (s). Distance traveled by impulsive litters was higher over normal litters. Treatment with LN16026F1 showed lesser locomotion in comparison with impulsive litters. Movement time (s) of impulsive litters was higher than Normal litters on days 7 and 14. Treatment with LN16026F1 showed lesser movement recorded in seconds in comparison with impulsive litters. Resting time of impulsive litters was marginally lesser on day 7 and day 14. Treatment with LN16026F1 could improve the resting time in comparison with impulsive litters as summarized in FIG. 2.

Burrowing activity was measured by offering a fixed quantity of sand in a PVC tube to litters of all the groups for 1 h and measuring the quantity of sand dug by each animal Burrowing behavior of the impulsive litters was significantly lower in comparison with normal litters. In litters of LN16026F3 treated group, showed significant improvement in burrowing behaviour as summarized in FIG. 3.

Example-10

Evaluation of LN16026F3 for Nootropic Activity (Learning and Memory Enhancement) in Morris Water Maze Twenty four healthy male Sprague Dawley rats were randomized in to four groups. Animals of groups 1 and 2 were treated daily with vehicle (0.5% sodium CMC in water); group 3 with LN16026F3 (100 mg/kg) and group 4 with Donepezil Hydrochloride Monohydrate (10 mg/kg). Dementia was induced by injecting Scopolamine Hydrobromide (0.2 mg/kg) subcutaneously to G2, G3 & G4 groups. G1 group received only 1 mL/kg of normal saline (0.9% w/v sodium chloride) via subcutaneous route.

The experiment consists of 4 days of acquisition trials and one probe trial on day 5 i.e. the day after the completion of acquisition trails. Rats were allowed to swim for 120 seconds of 4 trials per day during acquisition trial in water maze to find the hidden platform. Each rat received 4 days of acquisition trials and one probe trial of 180 seconds on day 5. The movement of the animals was tracked by the SMART video tracking system. Memory retention was assessed on day 5 in which each animal received a single 180 seconds probe trial without platform in the pool. Dopamine levels were measured in tissue from hippocampal region of the brain using Elisa kit.

Results

Oral supplementation of LN16026F3 (100 mg/kg body weight, for 4 days) resulted in significant reduction of latency to reach platform and shortened the path to reach platform. This decreased the target latency indicate that LN16026F3 is enhancing learning ability. Oral treatment with Donepezil (G4—10 mg/kg) also exhibited reduction in target latency. LN16026F3 treatment resulted in improved hippocampal dopamine levels, this further indicates memory improvement and improved brain functions. Results are summarized in FIG. 4.

On day 5, retention of memory was assessed using probe trial. LN16026F3 exhibited more retention of memory and spend more time in target quadrant, reduction in time to reach target and made more number of crossings over the target (location of platform in acquisition trial). Increased number of crossings and time spend in target quadrant indicate that treated animals have better retention of memory. Results are summarized in FIG. 5

In conclusion, oral administration of LN16026F3 improves learning and memory retention. LN16026F3 also protects from dementia.

We claim:

1. An herbal composition comprising:
an effective amount of an extract of *Bacopa monnieri*; and
an effective amount of an extract of *Terminalia chebula* fruit;
wherein the herbal composition is effective for at least one of:
enhancing memory;
enhancing cognition; and
treating a cognition or memory deficit; and
wherein the extract of *Bacopa monnieri* and the extract of *Terminalia chebula* fruit are present in a ratio ranging from 1:3 to 3:1.

2. The herbal composition as claimed in claim 1, further comprising at least one component selected from the group consisting of:
a pharmaceutically or nutraceutically or dietically acceptable excipient, carrier, or diluent;
a biological agent;
an antioxidant,
an anti-inflammatory agent, an immune modulator; and
a nootropic agent.

3. The herbal composition as claimed in claim 2, wherein the pharmaceutically or nutraceutically or dietically acceptable excipient, carrier, or diluent is selected from the group consisting of glucose, fructose, sucrose, maltose, yellow dextrin, white dextrin, aerosil, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, proteins, calcium salts, pigments, flavors, preservatives, distilled water, saline, aqueous glucose solution, alcohol, propylene glycol and polyethylene glycol, various animal and vegetable oils, white soft paraffin, paraffin, flavorants, colourants, wax, and a mixture thereof.

4. The herbal composition as claimed in claim 2, wherein the herbal composition is formulated into a dosage form.

5. The herbal composition as claimed in claim 4, wherein the dosage form is selected from the group consisting of a dry powder, a liquid, a beverage, a food product, a dietary supplement, a tablet, a capsule, a soft chewable form, and a gummy candy.

6. The herbal composition as claimed in claim 2, wherein the herbal composition is formulated into a solid food, a semisolid food, a beverage, a drop, a candy, a chewing gum, a gummy candy, yoghurt, ice cream, pudding, soft adzuki bean jelly, a jelly, a cookie, a tea, a soft drink, a juice, milk, coffee, a cereal, or a snack bar.

7. The herbal composition as claimed in claim 2, wherein the herbal composition is formulated into:
a solid food selected from the group consisting of a chocolate bar and a nutritional bar;
a semisolid food selected from the group consisting of a cream, a jam, a gel; or
a beverage; or
a lactic acid bacteria beverage.

8. An herbal composition comprising:
an effective amount of an extract of *Bacopa monnieri*; and
an effective amount of an extract of *Terminalia chebula*;
wherein the herbal composition is effective for at least one of enhancing memory, enhancing cognition, and treating a cognition or memory deficit;
wherein the extract of *Bacopa monnieri* and the extract of *Terminalia chebula* are present in a ratio ranging from 1:3 to 3:1; and
wherein the extract of *Bacopa monnieri* contains from 20% to 70% total bacosides, based on an analysis by UV spectroscopy.

9. The herbal composition as claimed in claim 1, wherein the extract of *Bacopa monnieri* contains from 5% to 25% total bacosides, based on an analysis by HPLC.

10. The herbal composition as claimed in claim 8, wherein the extract of *Terminalia chebula* contains from 20% to 80% total polyphenols, based on an analysis by UV spectroscopy.

11. An herbal composition comprising:
an effective amount of an extract of *Bacopa monnieri*; and
an effective amount of an extract of *Terminalia chebula* fruit;
wherein the herbal composition is effective for at least one of enhancing memory, enhancing cognition, and treating a cognition or memory deficit;
wherein the extract of *Bacopa monnieri* and the extract of *Terminalia chebula* fruit are present in a ratio ranging from 1:3 to 3:1; and
wherein the extract of *Terminalia chebula* fruit contains at least one of:
1 to 6% total chebulagic acids;
1-12% total chebulinic acid;
1 to 10% ellagic acid; and
1 to 10% gallic acid,
based on an analysis by HPLC.

12. The herbal composition as claimed in claim 1, wherein the extract of *Bacopa monnieri* is obtained from at least one plant part selected from the group consisting of a fruit, aerial parts or leaves, a whole plant, and a mixture thereof.

13. The herbal composition as claimed in claim 1, wherein the extracts of *Bacopa monnieri* and *Terminalia chebula* fruit are prepared using a solvent selected from the group consisting of a C1-C5 alcohol; a ketone; a chlorinated solvent; water; C1-C7 hydrocarbons; esters; and mixtures thereof.

14. The herbal composition as claimed in claim 1, wherein the extracts of *Bacopa monnieri* and *Terminalia chebula* fruit are prepared using a solvent selected from the group consisting of ethanol, methanol, n-propanol, isopropyl alcohol, acetone, methyl isobutyl ketone, methylene dichloride, chloroform, water, hexane, ethyl acetate, and mixtures thereof.

15. An herbal composition comprising:
   from 25% to 75% by weight of an extract of *Bacopa monnieri*, wherein the extract of *Bacopa monnieri* contains from 20% to 70% total bacosides, based on an analysis by UV spectroscopy; and
   from 25% to 75% by weight of an extract of *Terminalia chebula*, wherein the extract of *Terminalia chebula* contains from 20% to 80% total polyphenols, based on an analysis by UV spectroscopy,
   based on the combined weight of the *Bacopa monnieri* and *Terminalia chebula* extracts;
   wherein the extract of *Bacopa monnieri* and the extract of *Terminalia chebula* are the only herbal ingredients in the herbal composition.

16. The herbal composition as claimed in claim 15, further comprising at least one component selected from the group consisting of:
   a pharmaceutically or nutraceutically or dietically acceptable excipient, carrier, or diluent;
   a biological agent;
   an antioxidant,
   an anti-inflammatory agent, an immune modulator; and
   a nootropic agent.

\* \* \* \* \*